United States Patent [19]

Thiem

[11] Patent Number: 5,782,572
[45] Date of Patent: Jul. 21, 1998

[54] POSITIONING DEVICE

[75] Inventor: Stefan Thiem, Heidelberg, Germany

[73] Assignee: Leica Instruments GmbH, Wetzlar, Germany

[21] Appl. No.: 795,850

[22] Filed: Feb. 5, 1997

[30] Foreign Application Priority Data

Feb. 5, 1996 [DE] Germany ............ 196 04 001.9

[51] Int. Cl.$^6$ ............................................. F16C 11/06
[52] U.S. Cl. ................... 403/90; 403/84; 403/322; 248/288.31; 83/915.5
[58] Field of Search ............ 403/83, 84, 90, 403/322; 248/288.31, 288.51, 181.1, 181.2; 83/915.5, 699.51

[56] References Cited

U.S. PATENT DOCUMENTS

| | | | |
|---|---|---|---|
| 1,166,018 | 12/1915 | Soresi | 248/181.1 X |
| 1,677,889 | 7/1928 | Gairing | 248/181.1 X |
| 1,766,555 | 9/1930 | Garbutt et al. | 248/181.2 |
| 3,211,405 | 10/1965 | Fey et al. | 248/181.1 X |
| 3,286,575 | 11/1966 | Burkhardt | 83/699.51 |
| 3,308,704 | 3/1967 | Burkhardt | 83/699.51 |
| 3,926,085 | 12/1975 | Shatzel | 83/915.5 X |
| 3,975,977 | 8/1976 | Mornberg | 83/707 |
| 5,072,907 | 12/1991 | Vogt | 248/181.1 |
| 5,082,254 | 1/1992 | Hunnell et al. | |
| 5,295,700 | 3/1994 | Crews et al. | 279/5 |
| 5,299,481 | 4/1994 | Lihl et al. | |
| 5,590,870 | 1/1997 | Goellner | 269/21 |

FOREIGN PATENT DOCUMENTS

| | | |
|---|---|---|
| 20 33 425 C3 | 4/1971 | Germany. |
| 2143529 | 3/1973 | Germany. |
| 8217700 U | 12/1982 | Germany. |
| 3714389 C1 | 6/1988 | Germany. |
| 3714411 C1 | 7/1988 | Germany. |
| 2182786 | 5/1987 | United Kingdom. |

OTHER PUBLICATIONS

"Operating Instructions: Kryostat 2800 Frigocut–E", Leica Instruments GmbH, pp. 34–36.

*Primary Examiner*—Daniel P. Stodola
*Assistant Examiner*—Bruce A. Lev
*Attorney, Agent, or Firm*—Foley & Lardner

[57] ABSTRACT

A positioning device, particularly for positioning an object head in a cryostat microtome, has a mechanism for selectively positioning an object or specimen to be worked upon. The device includes a ball and socket joint having two spherical half shells pivotally holding the ball between the shells. An object head is connected to the ball. A clamp is operatively associated with the two spherical half shells to maintain the ball in position relative to the shells. A cross-joint is connected to the ball, diametrically opposite to the object head. The positioning mechanism includes rotatably geared or threaded members controlled with handles to independently position the object head in the x- and y-directions or paths.

16 Claims, 2 Drawing Sheets

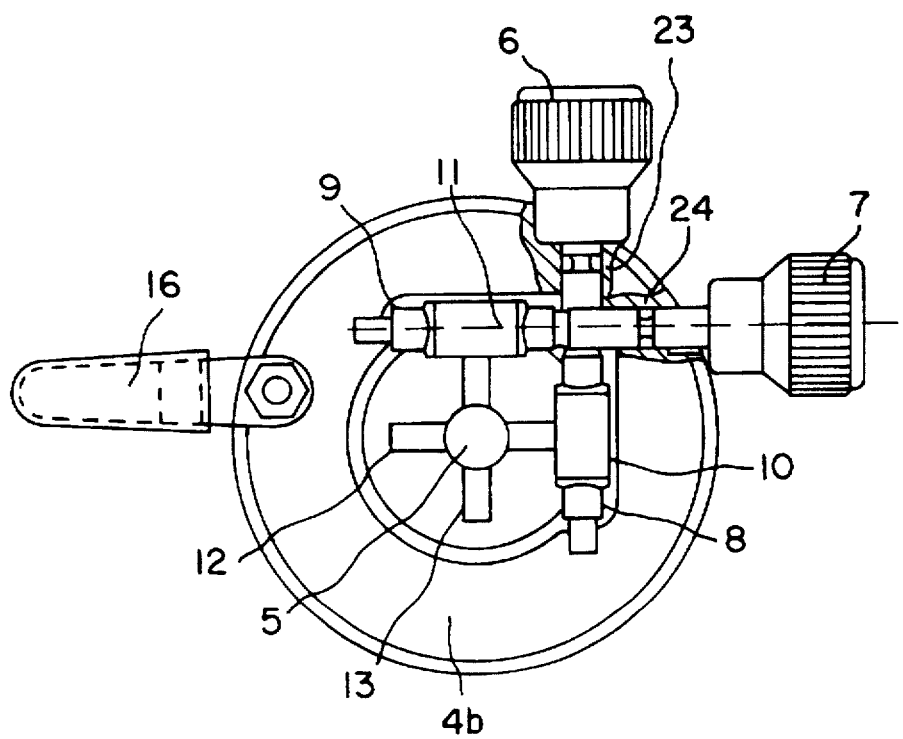

POSITIONING DEVICE

BACKGROUND OF THE INVENTION

An object-orienting device, such as LEICA CM 3000, is typically used to orient or position an object head that holds an article or specimen to be cut. The object head can be cooled. The object head is oriented or positioned with respect to a cutting blade in a cryostat microtome (e.g., LEICA CM 3000). In this cryostat microtome, the object head, which holds the specimen to be cut, is positioned by means of a ball and socket joint. The ball and socket joint has a ball movably mounted in the x- and y-directions between two spherical half shells. The ball and socket joint is clamped by means of a tightening lever that presses or urges one of the spherical half shells against the ball.

The object head is oriented or positioned through a pivot lever connected directly to the ball. The object head can be moved in the x- and y-directions by pivoting this lever. After setting the object head to the desired x- and y-positions, the tightening lever must be actuated at the same time to lock or clamp the ball in place due to the great weight of the object head, with its associated coolant hose.

This manner of setting the object head has been successful wherever a rapid head orientation is required. Due to the great weight of the object head, however, it is necessary to operate both the clamping and pivoted levers at the same time during the x- and y-position settings. Certain orientation tolerances thus must be accepted. Accordingly, there is a need for a way to more precisely orient or position such an object head, for instance, in a cryostat microtome. The present invention meets this need.

SUMMARY OF THE INVENTION

One aspect of the invention is a device for positioning an object head in a cryostat microtome. The positioning device includes a ball and socket joint, an object head, a clamp, a cross-joint, and a rotatable mechanism for positioning the object head. Specifically, the ball and socket joint has a ball and a shell rotatably or pivotally holding the ball. The clamp is connected to the shell to prevent the ball from moving relative to the shell. The cross-joint and the object head are connected to the ball so that these elements can move as a unit. The rotatable mechanism can move a first portion of the cross-joint along a first path or general direction and a second portion of the cross-joint along a second path or general direction, which is substantially perpendicular to the first path, to thereby selectively move the ball and position the object head connected thereto.

The shell can comprise a pair of spherical half shells. The clamp can include a gripping lever selectively operable to close the two spherical half shells and clamp the ball in place relative to the spherical half shells.

The rotatable mechanism can include two rotatable handles, each having associated gearing means, to move the first and second portions of the cross-joint substantially along the first and second paths respectively, the rotatable handles being positioned perpendicularly to each other. The handles can each include a threaded spindle rotatably mounted to one of the spherical half shells. Each gearing means can comprise the threaded spindle and a nut movably received in the threaded spindle, the nut being connected to the cross-joint. Specifically, each nut can have a pin and the cross-joint can have two elongated holes so that each pin can extend through one of the elongated holes. The two elongated holes extend perpendicularly to one another through the cross-joint.

In another aspect of the invention, the rotatable mechanism includes a first spindle rotatably mounted to the shell. The first spindle has a first movable member that moves along the first spindle in response to rotation of the first spindle. The first movable member is connected to the first portion of the cross-joint so that the first portion of the cross-joint moves in the same general path or direction as the movement of the first movable member.

The rotatable mechanism further includes a second spindle rotatably mounted to the shell. The second spindle, which can be perpendicular to the first spindle, has a second movable member that moves along the second spindle in response to rotation of the second spindle. The second movable member is connected to the second portion of the cross-joint so that the second portion of the cross-joint moves in the same general path or direction as the movement of the second movable member. Thus, the object head moves substantially in the opposite direction of the movement of the first and second movable members.

The first movable member can have a first pin extending perpendicularly to the first spindle and the second movable member can have a second pin extending perpendicularly to the second spindle. These first and second pins are used to move the cross-joint. In this respect, the cross-joint can have two perpendicularly extending holes, each pin extending through one of these holes.

Each of the first and second spindles can be threaded and each of the first and second moving members can have a complementary threading for receiving the respective threaded spindle. The first and second threaded spindles each can have a retainer to prevent them from moving in an axial direction of the spindles. Each of the first and second threaded spindles can have a handle that can be gripped and rotated to control the movement of the first and second moving members.

Another aspect of the invention is a more generic positioning device, which similarly includes a ball and a shell holding the ball. The ball is rotatably movable relative to the shell. The device includes a platform adapted to hold an object. Again, a clamp is operatively connected to the shell to prevent the ball from moving relative to the shell. The platform is connected to the ball so that it can be moved with the ball. A cross-joint is connected to the ball diametrically opposite to the platform. A rotatable mechanism is connected to the cross-joint to selectively move the platform by controlling movement of the cross-joint.

The rotatable mechanism can include first and second threaded spindles each rotatably mounted to the shell. A first threaded nut can be movably received on the first threaded spindle so that it moves along the first threaded spindle in response to its rotation. The first threaded nut can have a first pin extending therefrom, which first pin extends through a first portion of the cross-joint.

Similarly, a second threaded nut can be movably received on the second threaded spindle so that it moves along the second threaded spindle in response to its rotation. The second threaded nut can have a second pin extending therefrom, which second pin extends through a second portion of the cross-joint. The first and second pins preferably extend perpendicularly to each other.

BRIEF DESCRIPTION OF THE DRAWINGS

These and other features, aspects, and advantages of the present invention will become more apparent from the following description, appended claims, and accompanying exemplary drawings, which are briefly described below.

FIG. 3 shows a partially sectioned rear plan view of the positioning device of FIG. 1.

DETAILED DESCRIPTION OF THE PREFERRED EMBODIMENTS

Although references are made below to directions in describing the structure, they are made relative to the drawings (as normally viewed) for convenience. The directions, such as front, rear, x, y, z, are not intended to be taken literally or limit the present invention in any form.

Figure 1:
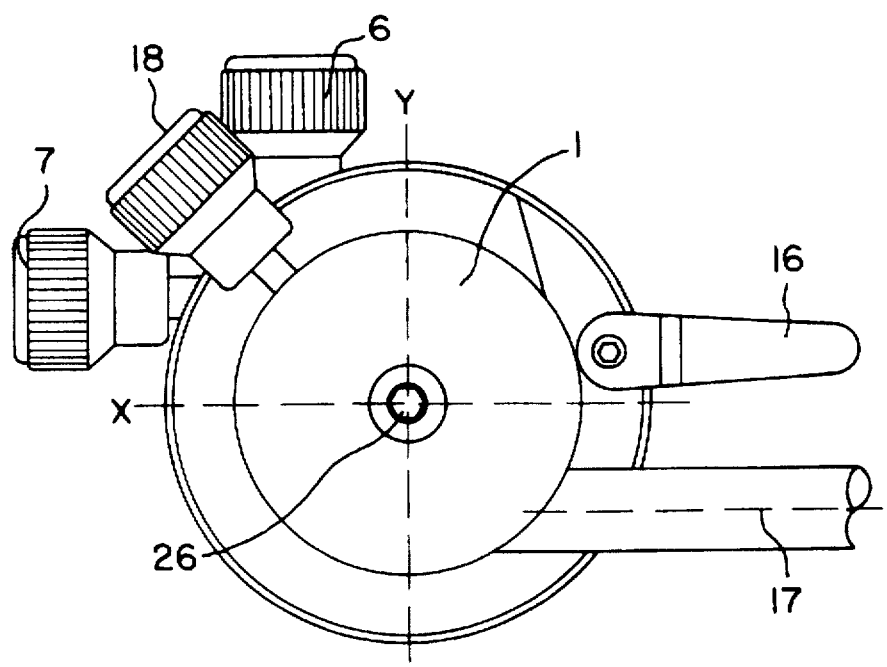
FIG. 1 shows a front plan view of a positioning device according to the present invention.
Figure 2:
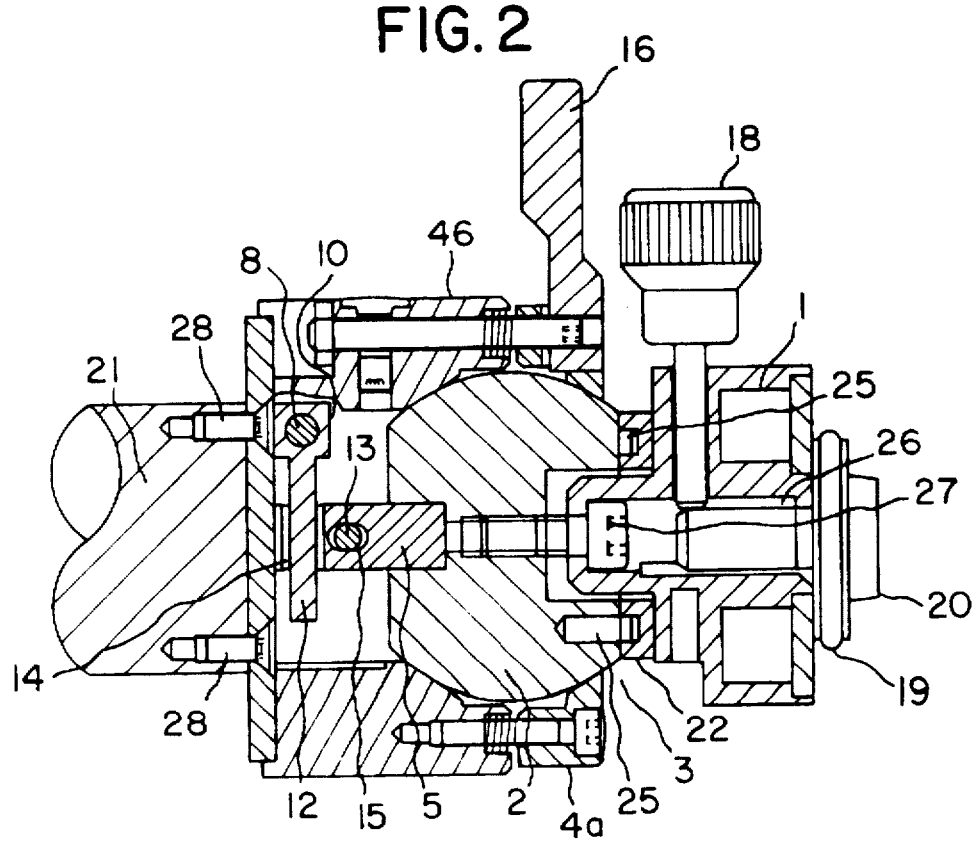
FIG. 2 shows a cross-sectional view of the positioning device of FIG. 1.

FIG. 1 shows a platform or object head 1 with a central bore 26 for receiving an object plate 19 (FIG. 2). A coolant hose 17 can be connected to the object head 1 to cool, with an associated cooling equipment, a specimen or object 20 (FIG. 2) held thereby to a prescribed or desired temperature.

A handle 18 for clamping the object plate 19 to the object head 1 is arranged at the object head 1. Two additional handles 6 and 7 serve to finely position and set the object head in the x- and y-directions. A clamp with a tightening lever 16 is provided for fixing the setting of the object head 1 and preventing movement thereof.

FIG. 2 shows a section through the object head 1 with the object plate 19 and the specimen or object 20 arranged thereupon. The object plate 19 is clamped in the object head 1 with the handle 18, for example, by rotating the handle, which has an associated threaded spindle, threadingly extending in the object head.

The object head 1 is connected to a centrally arranged ball 2 via two aligning pins 25 and a screw 27. The object head 1 has an insulation member 22 on which the aligning pins are inserted. The insulation member 22 thermally insulates the object head from the ball. The ball 2 is rotatably guided between a shell, preferably two spherical half shells 4a and 4b, which together with the ball 2 form a ball and socket joint 3. The lever 16 presses the spherical half shell 4a against the other spherical half shell 4b to fix or clamp the ball 2 in its position. The spherical half shell 4b is connected to a cylinder 21 of a microtome using screws 28. The cylinder 21 is movable up and down (e.g., z-direction).

A cross-joint 5 is connected to the ball 2, preferably diametrically opposite to the object head 1, as shown in FIG. 2. The cross-joint 5 has two perpendicularly extending elongated holes 14 and 15 that guide two perpendicularly extending pins 12 and 13 associated with the handles 6 and 7 for positioning the object head 1. The two elongated holes 14 and 15 are spaced apart in the longitudinal direction (e.g., z-direction) of the cross-joint 5 and permit the pins 12 and 13 to move or slide along their axial direction relative to the cross-joint 5.

FIG. 3 further shows the rotatable mechanism for positioning the object head 1, with fine adjustment capability, which mechanism includes the two handles 6 and 7 arranged perpendicularly to one another. Each handle 6, 7 is preferably permanently connected to a respective geared or threaded spindle 8, 9. Each threaded spindle 8, 9 is rotatably mounted or journaled in the spherical half shell 4b. A retainer 23, 24, such as a clip or safety lock, is respectively provided in each threaded spindle 8, 9 to prevent or secure the threaded spindles 8 and 9 from axially moving. Movably running on each threaded spindle 8, 9 respectively is a movable member, such as geared or threaded nut 10, 11, on which a respective pin 12, 13 is formed, preferably integrally therewith. Each pin 12, 13 extends laterally from the respective nut 10, 11, which is movably connected to the respective threaded spindle 8, 9. The threaded spindles 8 and 9 extend perpendicularly to each other, as do the pins 12 and 13. Thus, the threaded spindle 8 and the pin 13 extend parallel with each other, as do the threaded spindle 9 and the pin 12.

Rotational movement of the handle 6, 7 is transferred to the nut 10, 11, via the spindle 8, 9. The nut 10, 11 then moves along the respective spindle 8, 9 together with the pin 12, 13. Thus, the longitudinal movement of the nut 10, 11 and thus of the pin 12, 13 extending through the cross-joint's elongated hole 14, 15 is transferred to the cross-joint 5 by way of the elongated holes 14, 15. Since the cross-joint 5 is connected, preferably permanently, to the ball 2, its movement causes pivoting or pitching movement of the ball 2 relative to the spherical half shells 4a, 4b, which pivoting movement shifts the object plate 19 arranged thereon substantially along the X- and y-paths (FIG. 1). That is, since the cross-joint 5 and the object head 1 are connected to the ball and positioned diametrically opposite to each other, the movement of the cross-joint 5 in one direction causes the object head 1 to move in the opposite direction substantially along the same x- and y-paths.

Rotating the handle 6 moves the pin 12, which extends parallel to the x-axis in the elongated hole 14, along the y-path, moving the object head in the opposite direction along the same y-path. Similarly, rotating the handle 7 moves the pin 13, which extends parallel to the y-axis in the elongated hole 15, along the x-path, moving the object head in the opposite direction along the x-path.

It is therefore possible using the present invention to align the object head, particularly of a microtome, separately and precisely along the x- or y-direction, or both directions simultaneously via a geared or threaded connection to ensure an optimum position for cutting of a specimen.

Given the disclosure of the present invention, one versed in the art would appreciate that there may be other embodiments and modifications within the scope and spirit of the present invention. Accordingly, all modifications attainable by one versed in the art from the present disclosure within the scope and spirit of the present invention are to be included as further embodiments of the present invention. The scope of the present invention accordingly is to be defined as set forth in the appended claims.

The disclosure of German priority application 19604001.9, filed Feb. 5, 1996, in its entirety, including the drawings, claims, and the specification thereof, is incorporated herein by reference.

I claim:

1. A device for positioning an object head in a cryostat microtome, comprising:

a ball and socket joint having a ball and a shell holding the ball, the ball being rotatable movable relative to the shell;

an object head connected to the ball;

a clamp connected to the shell for preventing movement of the ball relative to the shell;

a cross-joint connected to the ball, the cross-joint having first and second portions; and a rotatable mechanism for moving the first portion of the cross-joint along a first path and the second portion of the cross-joint along a second path, which is substantially perpendicular to the first path, to thereby selectively move the ball and position the object head connected thereto, wherein the rotatable mechanism comprises two rotatable handles, each having gearing means, to move the first and second portions of the cross-joint substantially along the first and second paths respectively, the rotatable handles being positioned perpendicularly to each other, and wherein each gearing means includes a threaded spindle rotatable mounted to the shell and a nut movably received in the threaded spindle, the nut being connected to the cross-joint at one of the first and second portions of the cross-joint.

2. A positioning device according to claim 1, wherein the shell comprises a pair of spherical half shells.

3. A positioning device according to claim 2, wherein the clamp includes a lever selectively operable to close the two spherical half shells and clamp the ball in place to prevent the ball from moving relative to the spherical half shells.

4. A positioning device according to claim 2, wherein the threaded spindle is rotatably mounted to one of the spherical half shells.

5. A positioning device according to claim 1, wherein each nut has a pin and the first and second portions of the cross-joint comprise two elongated holes, each pin extending through one of the elongated holes.

6. A positioning device according to claim 5, wherein the two elongated holes extend perpendicularly to one another through the cross-joint.

7. A device for positioning an object head in a cryostat microtome, comprising:

a ball and socket joint having a ball and a shell holding the ball, the ball being rotatable movable relative to the shell;

an object head connected to the ball;

a clamp connected to the shell for preventing movement of the ball relative to the shell;

a cross-joint connected to the ball, the cross-joint having first and second portions;

a rotatable mechanism for moving the first portion of the cross-joint along a first path and the second portion of the cross-joint along a second path, which is substantially perpendicular to the first path, to thereby selectively move the ball and position the object head connected thereto, wherein the rotatable mechanism includes a first spindle rotatably mounted to the shell, the first spindle having a first movable member that moves along the first spindle in response to rotation of the first spindle, the first movable member being connected to the first portion of the cross-joint, wherein the first portion of the cross-joint moves in a same general path as the movement of the first movable member, and wherein the rotatable mechanism further includes a second spindle rotatably mounted to the shell, the second spindle having a second movable member that moves along the second spindle in response to rotation of the second spindle, the second movable member being connected to the second portion of the cross-joint, wherein the second portion of the cross-joint moves in a same general path as the movement of the second movable member.

8. A positioning device according to claim 7, wherein the first spindle is perpendicular to the second spindle.

9. A positioning device according to claim 8, wherein the object head moves substantially in an opposite direction of the movement of the first and second movable members.

10. A positioning device according to claim 9, wherein the first movable member has a first pin extending perpendicularly to the first spindle and the second movable member has a second pin extending perpendicularly to the second spindle, the first and second pins being connected to the cross-joint.

11. A positioning device according to claim 10, wherein the cross-joint has two perpendicularly extending holes, each pin extending through one of the holes.

12. A positioning device according to claim 7, wherein each of the first and second spindles is threaded and each of the first and second moving members has a complementary threading for receiving the respective threaded spindle.

13. A positioning device according to claim 12, wherein the first and second threaded spindles each have a retainer for preventing the spindles from moving in an axial direction of the spindles.

14. A positioning device according to claim 12, wherein each of the first and second threaded spindles has a handle adapted to be gripped and rotated to control the movement of the first and second moving members.

15. A positioning device comprising:

a ball;

a shell holding the ball, the ball being rotatably movable relative to the shell;

a platform adapted to hold an object, the platform being connected to the ball so as to be movable with the ball;

a clamp operatively connected to the shell for selectively preventing movement of the ball relative to the shell;

a cross-point connected to the ball diametrically opposite to the platform;

a rotatable mechanism connected to the cross-joint for selectively moving the platform by controlling movement of the cross-joint, wherein the rotatable mechanism includes first and second threaded spindles each rotatably mounted to the shell, a first threaded nut movable along the first threaded spindle in response to rotation of the first threaded spindle, the first threaded nut having a first pin extending therefrom, which first pin extends through a first portion of the cross-joint, and a second threaded nut movable along the second threaded spindle in response to rotation of the second threaded spindle, the second threaded nut having a second pin extending therefrom, which second pin extends through a second portion of the cross-joint.

16. A positioning device according to claim 15, wherein the first and second pins extend perpendicularly to each other.

* * * * *